US005767961A

United States Patent [19]
Nishikawa et al.

[11] Patent Number: 5,767,961
[45] Date of Patent: Jun. 16, 1998

[54] APPARATUS AND METHOD FOR INSPECTING FLUORESCENT SCREEN

[75] Inventors: Shigeharu Nishikawa; Kenichi Matsumura, both of Shiga, Japan

[73] Assignee: NEC Corporation, Tokyo, Japan

[21] Appl. No.: 637,285

[22] Filed: Apr. 24, 1996

[30] Foreign Application Priority Data

Apr. 25, 1995 [JP] Japan .................... 7-099299
Nov. 30, 1995 [JP] Japan .................... 7-312220

[51] Int. Cl.$^6$ .................................... G01N 21/00
[52] U.S. Cl. ................... 356/237; 356/239; 356/430; 356/431
[58] Field of Search .................... 356/237, 239, 356/371, 430, 431; 250/559.45, 559.48

[56] References Cited

U.S. PATENT DOCUMENTS

| | | | |
|---|---|---|---|
| 3,835,332 | 9/1974 | Bridges | 356/430 |
| 4,076,426 | 2/1978 | Gross et al. | 356/239 |
| 5,243,402 | 9/1993 | Weber et al. | 356/430 |
| 5,305,080 | 4/1994 | Lee et al. | 356/239 |
| 5,459,330 | 10/1995 | Venaille et al. | 356/239 |

FOREIGN PATENT DOCUMENTS 60-160539  8/1985  Japan .
1-183031   7/1989  Japan .

*Primary Examiner*—Frank G. Font
*Attorney, Agent, or Firm*—Sughrue, Mion, Zinn, Macpeak & Seas, PLLC

[57] ABSTRACT

The present invention provides an apparatus for inspecting a fluorescent screen, including a line light source for radiating light onto an external surface of a panel formed at an internal surface thereof with a fluorescent screen, a line sensor disposed facing to the internal surface of the panel for detecting light emitted from the line light source and transmitted through the fluorescent screen, a device for varying the relative positional relationship between the panel and a combination of the line light source and the line sensor in a direction perpendicular to a length-wise direction of the line sensor, and a processor for comparing linear patterns detected by the line sensor to a reference pattern. The apparatus automatically inspects an entire fluorescent screen, and further automatically makes judgement as to whether the fluorescent screen is good or bad in quality. In addition, the apparatus can eliminate Moiré fringes which would have been generated by fluctuation in the level of transmitted light to thereby make no misjudgment.

17 Claims, 4 Drawing Sheets

APPARATUS AND METHOD FOR INSPECTING FLUORESCENT SCREEN

BACKGROUND OF THE INVENTION

1. Field of the Invention

The invention relates to an apparatus and a method for inspecting a fluorescent screen of a cathode ray tube, and more particularly to such an apparatus and a method ensuring higher accuracy in inspection by adjusting the angular position of a line sensor.

2. Description of the Related Art

In general, a shadow mask type color cathode ray tube includes a panel formed on an internal surface thereof with a black matrix film composed of light-absorbing material in facing relation to a shadow mask disposed inside the panel. The black matrix is formed at an opening thereof with a fluorescent screen composed of regularly arranged fine dot-shaped or fine stripe-shaped fluorescent layers which emit red, green or blue lights. The fluorescent screen is inspected as to whether foreign material is adhered thereto and whether it is desirably formed without defects such as irregular color in order to prevent inferior panels from being transferred to subsequent steps.

For instance, Japanese Unexamined Patent Publications Nos. 60-160539 and 1-183031 have suggested the attempts for inspecting a fluorescent screen, in which an ultraviolet ray is radiated onto a fluorescent screen to thereby excite the fluorescent substance so that it emits light, and the fluorescent screen is visually inspected by means of a microscope.

Since foreign material adhered to a fluorescent screen and/or irregular color of a fluorescent screen can be found with naked eyes through transmitted light, the inspection of a fluorescent screen is in general, visually carried out by radiating an ultraviolet ray at a fluorescent screen. More specifically, as illustrated in FIG. 1, a white light source or ultraviolet ray source 13 is disposed below a fluorescent screen 2 formed on an internal surface of a panel 1, and an operator 14 looks at light 15 emitted from the light source 13 and transmitting through the fluorescent screen 2 using eyesight from above the panel 1 to thereby identify sun spots and/or luminescent spots of the fluorescent screen 2.

However, there arise differences between individuals in the above described visual inspection by an operator. In addition, it is not possible by the prior art to entirely inspect a fluorescent screen, and thus inferior panels may not be found. Furthermore, perfect inspection to be manually carried out by an operator would take too much time. Thus, it is desired that the inspection is automated.

These days, a color display to be used for a computer has been shifted to a highly accurate, fine pixel type due to development in performance and multi-functions in the field of communication and image-processing. It is necessary to enhance accuracy and efficiency in panel inspection in order to respond to such a development in a color display.

SUMMARY OF THE INVENTION

In view of the earlier mentioned problems in the prior art, it is an object of the present invention to provide an apparatus and a method for automatically inspecting an entire fluorescent screen and automatically making judgement as to whether a fluorescent screen is good or bad in quality.

In one aspect, the present invention provides an apparatus for inspecting a fluorescent screen, including a line light source for radiating light onto an external surface of a panel formed at an internal surface thereof with a fluorescent screen, a line sensor disposed facing to the internal surface of the panel for detecting light emitted from the line light source and transmitting through the fluorescent screen, a device for varying relative positional relationship between the panel and a combination of the line light source and the line sensor in a direction perpendicular to a length-wise direction of the line light source, and a processor for comparing linear patterns detected by the line sensor to a reference pattern.

For instance, the line light source may emit white light or an ultraviolet ray, in which case the linear patterns include transmitted light patterns or emission patterns to be obtained by exciting a fluorescent substance, respectively.

It is preferable for the processor to have a device for smoothing image data. The device for varying a relative positional relationship between the panel and a combination of the line light source and the line sensor may move either the above panel or the combination of the line light source and the line sensor in the direction.

It is preferable for the apparatus to further have an auxiliary line sensor disposed facing to the external surface of the panel for detecting light reflected by the fluorescent screen. It is also preferable for the apparatus to further have an adjuster for minimizing an angle formed between the picture elements arrangement of the auxiliary line sensor and dot arrangement of the fluorescent screen. For instance, the adjuster may be constituted of a pulse or stepping motor to rotate the auxiliary line sensor about a center thereof.

The present invention further provides an apparatus for inspecting a fluorescent screen, including a line light source for radiating light onto an external surface of a panel formed at an internal surface thereof with a fluorescent screen, a line sensor disposed facing to the internal surface of the panel for detecting light emitted from the line light source and transmitting through the fluorescent screen, a device for varying relative positional relationship between the panel and a combination of the line light source and the line sensor in a direction perpendicular to a length-wise direction of the line light source, a processor for comparing linear patterns detected by the line sensor to a reference pattern, and an adjuster for minimizing an angle formed between the picture elements arrangement of the line sensor and dot arrangement of the fluorescent screen.

The adjuster may be constituted of a pulse or stepping motor to rotate the line sensor about a center thereof. It is preferable to design the processor so that it detects Moiré fringes of the linear patterns and causes the adjuster to stop rotation of the line sensor in accordance with the number of the thus detected Moiré fringes.

In another aspect, the present invention provides a method of inspecting a fluorescent screen, including the steps of (a) varying the relative positional relationship between a panel formed at an internal surface thereof with a fluorescent screen, and a combination of a line light source for radiating light onto an external surface of the panel, and a line sensor disposed facing to the internal surface of the panel, for detecting light emitted from the line light source and transmitting through the fluorescent screen, in a direction perpendicular to a length-wise direction of the line light source, with the line light source radiating light to the panel and also with the line sensor receiving light emitted from the line light source and transmitting through the fluorescent screen to read out linear patterns represented by the thus received light, (b) comparing the linear patterns to a reference pattern, and (c) judging as to whether a difference between the linear patterns and reference pattern is within an allowable range.

The method may preferably further include the steps of (d) counting the number of Moiré fringes in the linear patterns detected by the line sensor, (e) rotating the line sensor about a center thereof by degrees to be determined in accordance with the thus counted number of Moiré fringes so that an angle formed between picture elements arrangement of the line sensor and dot arrangement of the fluorescent screen is minimized, and (f) carrying out the step (a) again. These steps (d), (e) and (f) are to be carried out subsequently to the step (b), but prior to the step (c).

The method may preferably further include the steps of (g) rotating an auxiliary line sensor disposed facing to the external surface of the panel for detecting light reflected by the fluorescent screen about a center thereof by degrees to be determined in accordance with the number of Moiré fringes so that an angle formed between the picture elements arrangement of the line sensor and dot arrangement of the fluorescent screen is minimized. This step (g) is to be carried out concurrently with the step (e) or subsequently to the step (e), but prior to the step (f).

The advantages obtained by the aforementioned present invention will be described hereinbelow.

In accordance with the present invention, it is possible to automatically inspect an entire fluorescent screen and further automatically judge whether the inspected fluorescent screen is good or bad in quality. In the present invention, a line sensor is rotated by quite small degrees to thereby be positioned in place so that an angle formed between the picture elements arrangement of a line sensor and dot arrangement of a fluorescent screen is minimized. Thus, the line sensor can read out linear patterns through transmitted light with the above mentioned angle being at a minimum, and input the read out linear pattern data to the processor in which the linear pattern data is compared to reference pattern data having been compensated with a curvature of a panel and stored in a memory, thereby the panel being judged as to whether it is good or bad in quality.

Accordingly, the present invention can eliminate Moiré fringes which would have been generated by fluctuation in the level of transmitted light, to thereby make no misjudgment, resulting in a higher accuracy in detection. In addition, the additional provision of an auxiliary line sensor for detecting reflected light as linear patterns enhances the ability for detecting fine sun spots which would be generated on a fluorescent screen, and also significantly enhances accuracy in inspection.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Preferred embodiments in accordance with the present invention will be explained hereinbelow with reference to the drawings.

Figure 1:
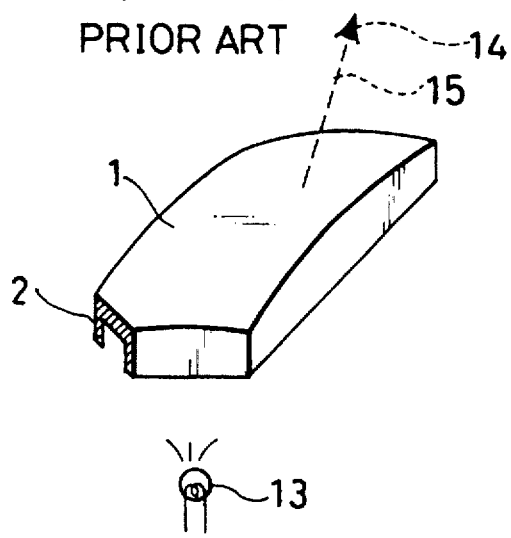
FIG. 1 is a schematic view illustrating a conventional apparatus for inspecting a fluorescent screen.
Figure 2:
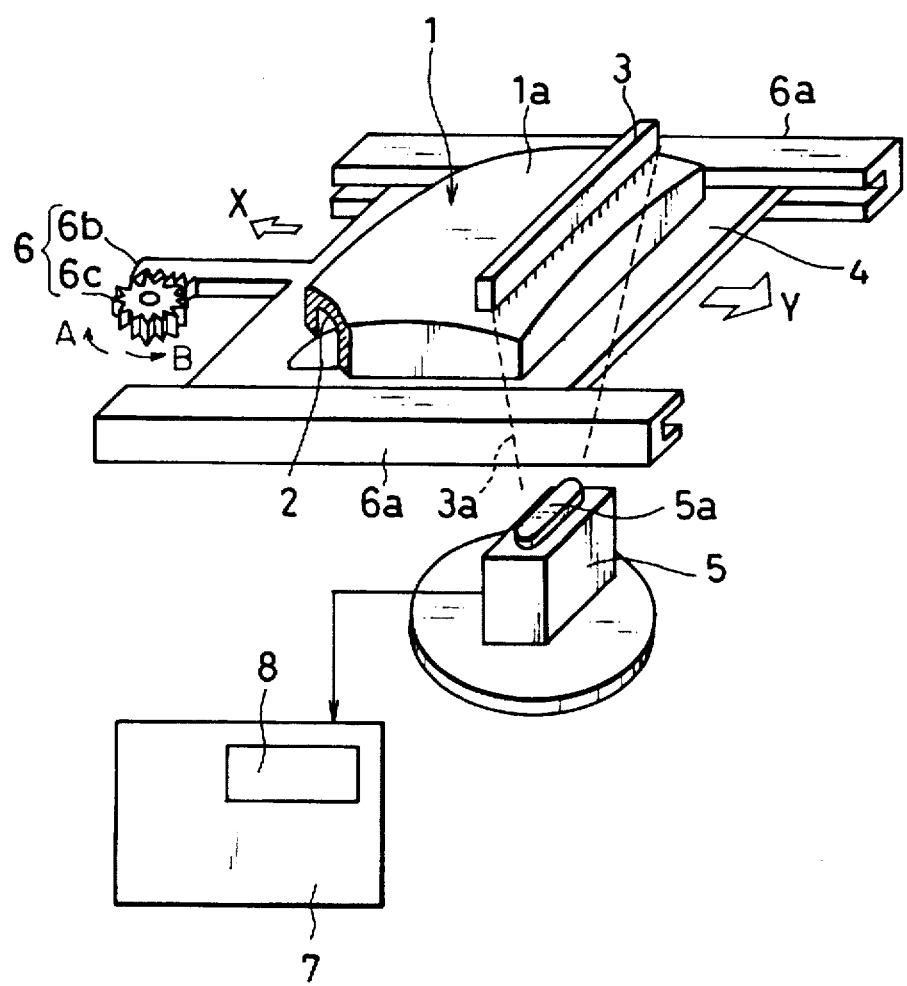
FIG. 2 is a schematic view illustrating an apparatus for inspecting a fluorescent screen made in accordance with the first embodiment of the present invention.

FIG. 2 illustrates an apparatus for inspecting a fluorescent screen fabricated in accordance with the first embodiment of the present invention. As illustrated, a panel 1 of a cathode ray tube is placed on a pallet 4. The panel 1 is formed on an internal surface thereof with a fluorescent screen 2. The fluorescent screen 2 is facing to the pallet 4, namely, the fluorescent screen 2 is not exposed outside.

Above the panel 1 is disposed a line light source 3 for radiating linear white light beam onto an external surface 1a of the panel. Below the pallet 4 is disposed a line sensor 5 in vertical alignment with the line light source 3 to receive light emitted from the line light source 3. The line sensor 5 has a light receiving section 5a which detects light 3a emitted from the line light source 3 and transmitted through the fluorescent screen 2 to thereby read out linear patterns represented with the transmitted light 3a.

The pallet 4 on which the panel 1 is placed is slidably supported at its opposite edges by a pair of U-shaped rails 6a, and is connected to a device 6 which varies the relative positional relationship between the panel 1 and a combination of the line light source 3 and the line sensor 5 in a direction Y or X perpendicular to a length-wise direction of the line light source 3. For instance, the device comprises a lack 6b connected to the pallet 4 and a pinion 6c in engagement with the lack 6b. The pinion 6c is fixedly connected to a motor (not illustrated). Thus, if the pinion 6c is rotated in a direction indicated with an arrow A the pallet 4 and hence the panel 1 slides along the rails 6a in the direction Y, whereas if the pinion 6c is rotated in a direction indicated with an arrow B, the pallet 4 and hence the panel 1 slides along the rails 6a in the direction X.

The line sensor 5 transmits signals representing the detected linear patterns to an image processor 7 for comparing the linear patterns to a reference pattern to thereby judge as to whether the fluorescent screen 2 is good or bad in quality. The image processor 7 includes a processor 8 for smoothing image data transmitted from the line sensor 5.

The apparatus for inspecting a fluorescent screen operates as follows. First, the line light source 3 emits white light beam onto a periphery of the fluorescent screen 2. The thus emitted white light beam transmits through the fluorescent screen 2 and is received as linear patterns by the light receiving section 5a of the line sensor 5. The data regarding the thus detected linear patterns is transmitted from the line sensor 5 to the image processor 7. The processor 8 for smoothing data eliminates noises included in the linear pattern data. Then, the linear pattern data is compared with data regarding a reference pattern stored in a memory (not illustrated). The reference pattern data stored in a memory has been in advance compensated with a curvature of the panel 1. The area of the fluorescent screen 2 to which the line light source 3 has emitted the white light beam is judged to be good in quality, if a difference between the linear pattern data and the reference pattern data is within an allowable range.

Then, the above mentioned inspection is repeated while the panel 1 is gradually moved by the device 6 in the direction Y, to thereby entirely inspect the fluorescent screen 2 for judging as to whether the entire fluorescent screen 2 is good or bad in quality.

Thus, the apparatus makes it possible to automatically, entirely inspect the fluorescent screens 2, and hence inferior fluorescent screen cannot be overlooked. Namely, since the apparatus automatically judges as to whether a fluorescent screen is good or bad in quality, it is no longer necessary for an operator to carry out a real inspection. In addition, the apparatus can carry out inspections in a shorter period of time than an operator.

The line light source 3 may be comprised of a mercury lamp which radiates ultraviolet rays. In such a case, since it is possible to observe linear patterns of the fluorescent screen 2 which would be excited an ultraviolet ray and emit light, the inspection of the fluorescent screen 2 can be carried out in the same operational condition as emission by electron beams. In addition, the inspection can be carried out, not visable by an operator, but by the line sensor 5 in automatic fashion.

Figure 5:
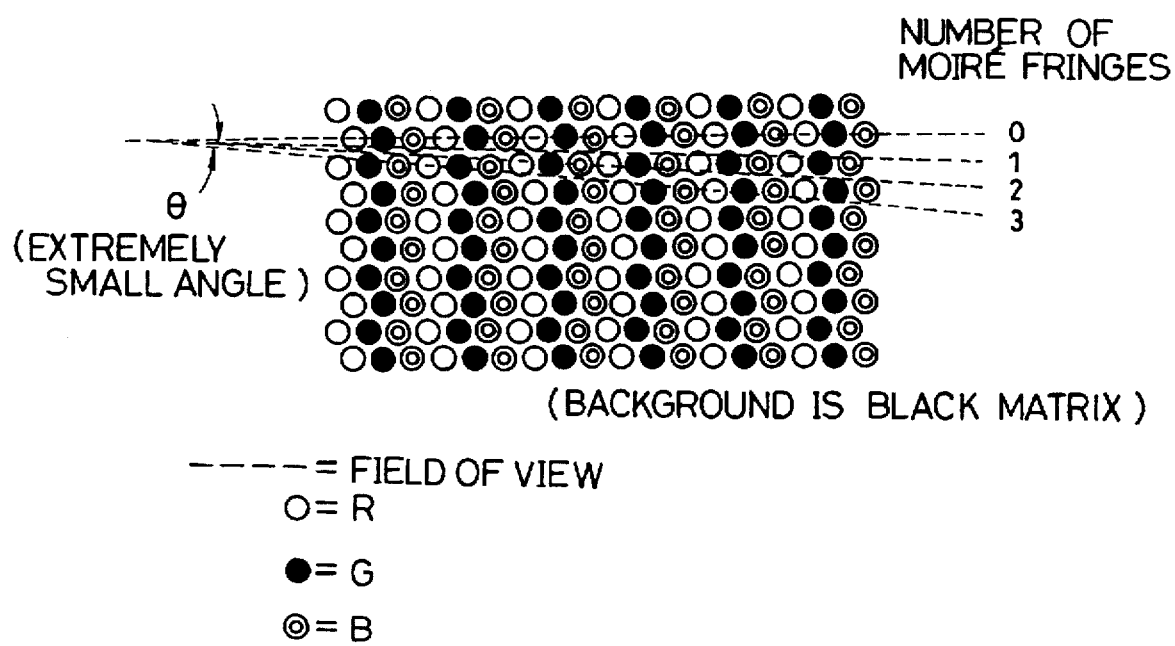
FIG. 5 is a schematic view showing the formation of Moiré fringes in an apparatus for inspecting a fluorescent screen.

In the above mentioned apparatus for inspecting a fluorescent screen fabricated in accordance with the first embodiment of the present invention, the panel 1 is designed to be move by the device 6 between the line light source 3 and the line sensor 5 in the direction Y or X perpendicular to a length-wise direction of the line light source 3. However, the dot arrangement of the fluorescent screen 2 is not always in parallel with the picture elements arrangement of the line sensor 5, and thus, there is formed a quite small angle θ between the dot arrangement of the fluorescent screen 2 and the picture elements arrangement of the line sensor 5. The presence of the quite small angle θ causes generation of a few numbers of Moiré fringes, as illustrated in FIG. 5. An amount of light to be transmitted through a fluorescent screen is fluctuated in dependence on the number of Moiré fringes, which results in that it is difficult to find defects in a fluorescent screen and thus the apparatus for inspecting a fluorescent screen may make misjudgments.

Thus, an apparatus for inspecting a fluorescent screen to be fabricated in accordance with the second embodiment of the present invention, which is to be explained hereinbelow, is designed to have means for minimizing an angle formed between the picture elements arrangement of the line sensor 5 and dot arrangement of the fluorescent screen 2 to thereby eliminate Moiré fringes to make it possible to detect minute defects in the fluorescent screen 2.

Figure 3:
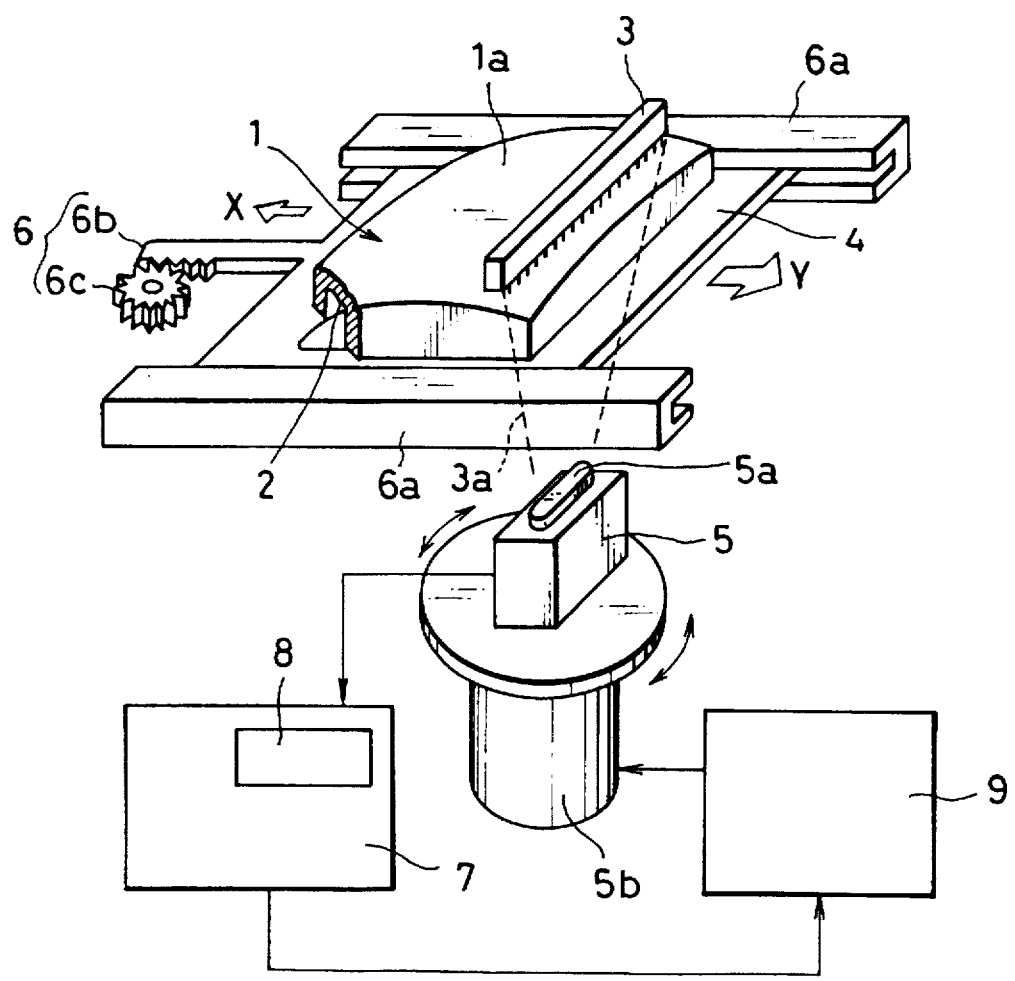
FIG. 3 is a schematic view illustrating an apparatus for inspecting a fluorescent screen made in accordance with the second embodiment of the present invention.

FIG. 3 illustrates an apparatus for inspecting a fluorescent screen to be fabricated in accordance with the second embodiment of the present invention. Parts or elements corresponding to those of the first embodiment illustrated in FIG. 2 have been provided with the same reference numerals, and will not be explained in detail. The apparatus of the second embodiment has the same structure as the apparatus of the first embodiment illustrated in FIG. 2 except that the second embodiment additionally includes an angle adjuster 5b and a controller 9. The angle adjuster 5b comprises a pulse or stepping motor for rotating the line sensor 5 by desired degrees in clockwise or counterclockwise direction. The controller 9 receives signals transmitted from the image processor 7, and establishes a rotation angle signal in accordance with the received signals from the image processor 7. The thus established rotation angle signal is transmitted to the angle adjuster 5b, and the angle adjuster 5b rotates the line sensor 5 by quite small degrees determined in accordance with the received rotation angle signal.

The apparatus to be fabricated in accordance with the second embodiment operates as follows. First, the line light source 3 emits white light beam onto the fluorescent screen 2. The thus emitted white light beam transmits through the fluorescent screen 2 and is received as linear patterns by the light receiving section 5a of the line sensor 5. The data about the thus detected linear patterns is transmitted from the line sensor 5 to the image processor 7. The processor 8 for smoothing data, eliminates noise included in the linear pattern data. The detection by the line sensor for the transmitted light is continued as the panel 1 placed on the pallet 4 is horizontally moved by the device 6 in the direction Y. Thus, the linear pattern data is continuously transmitted to the image processor 7, and analyzed in the image processor 7.

Specifically, the image processor 7 counts the number of Moiré fringes contained in the images represented by the linear pattern data detected by and transmitted from the line sensor 5. For instance, the line sensor 5 may include a plurality of charged coupled devices (CCDs) for detecting such data. The image processor transmits a signal representing the number of the counted Moiré fringes to the controller 9, which in turn establishes a rotation angle signal in accordance with the number of the Moiré fringes so that an angle formed between the picture elements arrangement of the line sensor 5 and the dot arrangement of the fluorescent screen 2 is minimized. The thus established rotation angle signal is transmitted from the controller 9 to the angle adjuster or pulse motor 5b to thereby cause the pulse motor 5 and hence the line sensor 5 to rotate by desired degrees in a desired direction.

Thus, the angle adjuster or pulse motor 5b rotates the line sensor 5 by quite small degrees to thereby position the line sensor 5 so that an angle formed between the picture elements arrangement of the line sensor 5 and the dot arrangement of the fluorescent screen 2 is minimized. Herein, the quite small degrees vary in dependence on the size of the color cathode ray tube, and in general, is about ±0.5 degrees relative to a reference degree of 0 degree.

After the line sensor 5 has been thus positioned in place, the panel 1 placed on the pallet 4 is horizontally moved by the device 6 in the direction Y or X. The line sensor 5 detects white light beam emitted from the line light source 3 and transmitted through the fluorescent screen 2 and reads out linear patterns indicated with the thus detected transmitted light. The data about the thus detected linear patterns is transmitted from the line sensor 5 to the image processor 7, and analyzed in the image processor 7. After the processor 8 for smoothing data eliminates noise included in the linear pattern data, the linear pattern data is compared with the reference pattern data stored in a memory (not illustrated). The reference pattern data stored in a memory has been in advance compensated with a curvature of the panel 1. The area of the fluorescent screen 2 to which the line light source 3 has emitted white light beam is judged to be good in quality, if a difference between the linear pattern data and the reference pattern data is within an allowable range.

Then, the above mentioned inspection is repeated while the panel 1 is gradually moved by the device 6 in the direction Y or X, to thereby entirely inspect the fluorescent screen 2 for judging as to whether the entire fluorescent screen 2 is good or bad in quality.

Thus, the apparatus makes it possible to automatically, entirely inspect the fluorescent screen 2 without misjudgements which would be caused by Moiré fringes.

Figure 4:
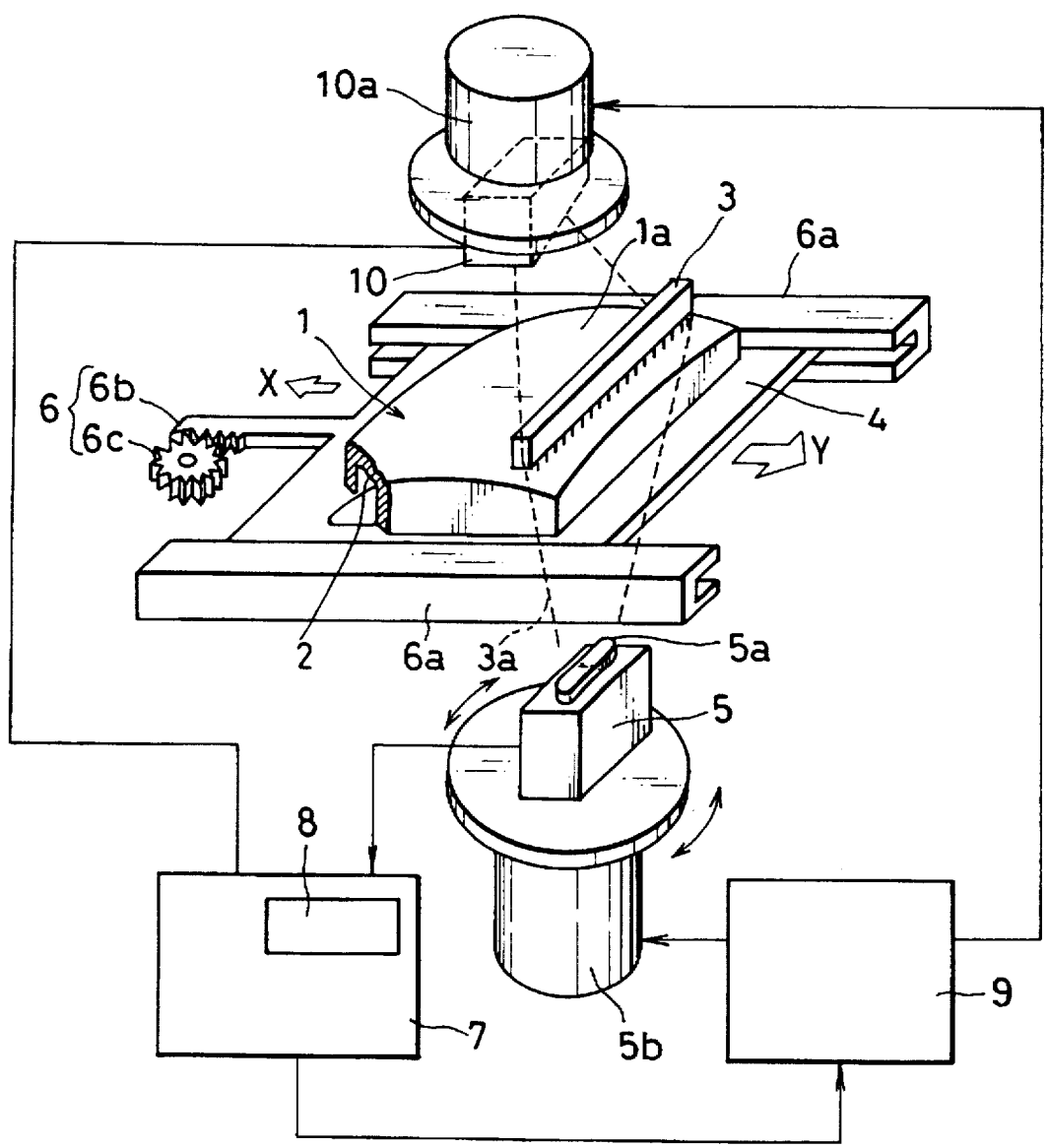
FIG. 4 is a schematic view illustrating an apparatus for inspecting a fluorescent screen made in accordance with the third embodiment of the present invention.

FIG. 4 illustrates an apparatus for inspecting a fluorescent screen to be fabricated in accordance with the third embodiment of the present invention. Parts or elements corresponding to those of the second embodiment illustrated in FIG. 3 have been provided with the same reference numerals, and will not be explained in detail. The apparatus of the third embodiment has the same structure as the apparatus of the second embodiment illustrated in FIG. 3 except that the third embodiment additionally includes an auxiliary line sensor 10 and an angle adjuster 10a for rotating the line sensor 10 by small degrees.

The line sensor 10a detects white light beam emitted from the line light source 3 and reflected at the external surface 1a of the panel 1. The line sensor 10 has the same structure as the line sensor 5, but may have a different structure from the line sensor 5 unless it can detect the reflected light. Similarly to the angle adjuster 5b, the angle adjuster 10a comprises a pulse or stepping motor for rotating the auxiliary line sensor 10 by desired degrees in a clockwise or counterclockwise direction. The angle adjuster 10a receives a rotation angle signal emitted from the controller 9, and rotates the auxiliary line sensor 10 by quite small degrees determined in accordance with the received rotation angle signal.

The apparatus to be fabricated in accordance with the third embodiment operates as follows. The apparatus operates in the same way as the second embodiment until the angle adjuster 5b rotates the line sensor 5a by quite small degrees determined in accordance with the rotation angle signal emitted from the controller 9 so that an angle formed between the picture elements arrangement of the line sensor 5 and the dot arrangement of the fluorescent screen 2 is minimized. A signal representing the thus minimized angle is also transmitted to the line adjuster 10a from the controller 9 to thereby rotate the auxiliary line sensor 10 by the angle so that an angle formed between the picture elements arrangement of the auxiliary line sensor 10a and the dot arrangement of the fluorescent screen 2 is minimized.

Then, the panel 1 is gradually, horizontally moved by means of the device 6. The line sensor 5 detects the transmitted light as linear patterns, and the auxiliary line sensor 10 detects the reflected light as linear patterns. These linear patterns detected by the line sensor 5 and auxiliary line sensor 10 are transmitted to the image processor 7, and analyzed in the image processor 7. After the processor 8 for smoothing data eliminates noise included in the linear pattern data, the linear pattern data is compared with the reference pattern data stored in a memory (not illustrated). The reference pattern data stored in a memory has been in advance compensated with a curvature of the panel 1. The area of the fluorescent screen 2 to which the line light source 3 has emitted a white light beam is judged to be good in quality, if a difference between the linear pattern data and the reference pattern data is within an allowable range.

Then, the above mentioned inspection is repeated while the panel 1 is gradually moved by the device 6 in the direction Y or X, to thereby entirely inspect the fluorescent screen 2 for judging as to whether the entire fluorescent screen 2 is good or bad in quality.

Thus, the apparatus makes it possible to automatically, entirely inspect the fluorescent screen 2. In addition, the inspection can be carried out based on both the transmitted light and reflected light detected through the line sensor 5 and the auxiliary line sensor 10, respectively. The provision of the auxiliary line sensor 10 for reading out the linear patterns of the reflected light enhances ability of detecting fine sun spots on the fluorescent screen 2. Accordingly, the apparatus provides higher accuracy in the inspection of a fluorescent screen.

In the above described first to third embodiments, the panel 1 placed on the pallet 4 is moved by the device 6. However, it should be noted that a combination of the line light source 3, the line sensor 5 and the auxiliary line sensor 10 may be synchronously moved in place of the panel 1.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An apparatus for inspecting a fluorescent screen, comprising:
   a line light source for radiating light onto an external surface of a panel formed at an internal surface thereof with a fluorescent screen;
   a line sensor disposed facing to said internal surface of said panel for detecting light emitted from said line light source and transmitted through said fluorescent screen;
   an auxiliary line sensor disposed facing to said external surface of said panel for detecting light reflected by said fluorescent screen;
   an adjuster for minimizing an angle formed between a picture elements arrangement of said auxiliary line sensor and a dot arrangement of said fluorescent screen;
   means for varying a relative positional relationship between said panel and a combination of said line light source and said line sensor in a direction perpendicular to a length-wise direction of said line light source; and
   a processor for comparing linear patterns detected by said line sensor to a reference pattern.

2. The apparatus as set forth in claim 1, wherein said line light source emits white light, and said linear patterns comprise transmitted light patterns.

3. The apparatus as set forth in claim 1, wherein said line light source emits ultraviolet ray, and said linear patterns comprise emission patterns to be obtained by exciting a fluorescent substance.

4. The apparatus as set forth in claim 1, wherein said processor includes a device for smoothing image data.

5. The apparatus as set forth in claim 1, wherein said means for varying the relative positional relationship between said panel and a combination of said line light source and said line sensor, moves said panel in said direction.

6. The apparatus as set forth in claim 1 wherein said adjuster rotates said auxiliary line sensor about a center thereof.

7. The apparatus as set forth in claim 6, wherein said adjuster comprises a pulse motor.

8. An apparatus for inspecting a fluorescent screen, comprising:
   a line light source for radiating light onto an external surface of a panel formed at an internal surface thereof with a fluorescent screen;
   a line sensor disposed facing to said internal surface of said panel for detecting light emitted from said line light source and transmitting through said fluorescent screen;
   means for varying the relative positional relationship between said panel and a combination of said line light source and said line sensor in a direction perpendicular to a length-wise direction of said line light source;
   a processor for comparing linear patterns detected by said line sensor to a reference pattern; and
   an adjuster for minimizing an angle formed between a picture elements arrangement of said line sensor and a dot arrangement of said fluorescent screen.

9. The apparatus as set forth in claim 8, wherein said adjuster rotates said line sensor about a center thereof.

10. The apparatus as set forth in claim 8, wherein said processor detects Moiré fringes of said linear patterns and causes said adjuster to stop rotation of said line sensor in accordance with the number of the thus detected Moiré fringes.

11. The apparatus as set forth in claim 8, wherein said adjuster comprises a pulse motor.

12. The apparatus as set forth in claim 8 further comprising an auxiliary line sensor disposed facing to said external surface of said panel for detecting light reflected by said fluorescent screen.

13. The apparatus as set forth in claim 12 further comprising an adjuster for minimizing an angle formed between a picture elements arrangement of said auxiliary line sensor and a dot arrangement of said fluorescent screen.

14. The apparatus as set forth in claim 13 wherein said adjuster rotates said auxiliary line sensor about a center thereof.

15. The apparatus as set forth in claim 14, wherein said adjuster comprises a pulse motor.

16. A method of inspecting a fluorescent screen, comprising the steps of:

(a) varying a relative positional relationship between a panel formed at an internal surface thereof with a fluorescent screen and a combination of a line light source for radiating light onto an external surface of said panel and a line sensor disposed facing to said internal surface of said panel for detecting light emitted from said line light source and transmitted through said fluorescent screen, in a direction perpendicular to a length-wise direction of said line light source, with said line light source radiating light to said panel and also with said line sensor receiving light emitted from said line light source and transmitted through said fluorescent screen to read out linear patterns represented by the thus received light;

(b) comparing said linear patterns to a reference pattern;

(c) judging as to whether a difference between said linear patterns and reference pattern is within an allowable range;

(d) counting the number of Moiré fringes in said linear patterns detected by said line sensor;

(e) rotating said line sensor about a center thereof by degrees to be determined in accordance with the thus counted number of Moiré fringes so that an angle formed between the picture elements arrangement of said line sensor and the dot arrangement of said fluorescent screen is minimized; and (f) carrying out said step (a) again, said steps (d), (e) and (f) being carried out subsequently to said step (b), but prior to said step (c).

17. The method as set forth in claim 16 further comprising the steps of:

(g) rotating an auxiliary line sensor disposed facing to said external surface of said panel for detecting light reflected by said fluorescent screen about a center thereof by degrees to be determined in accordance with said number of Moiré fringes so that an angle formed between the picture elements arrangement of said line sensor and the dot arrangement of said fluorescent screen is minimized, said step (g) being to be carried out concurrently with said step (e) or subsequently to said step (e), but prior to said step (f).

* * * * *